(12) United States Patent
Kelly et al.

(10) Patent No.: US 7,884,323 B2
(45) Date of Patent: Feb. 8, 2011

(54) ATOM PROBES, ATOM PROBE SPECIMENS, AND ASSOCIATED METHODS

(75) Inventors: Thomas F. Kelly, Madison, WI (US);
Joseph H. Bunton, Madison, WI (US);
Scott A. Wiener, Mount Horeb, WI (US)

(73) Assignee: Cameca Instruments, Inc., Mahwah, NJ (US)

( * ) Notice: Subject to any disclaimer, the term of this patent is extended or adjusted under 35 U.S.C. 154(b) by 371 days.

(21) Appl. No.: 12/064,020

(22) PCT Filed: Aug. 15, 2006

(86) PCT No.: PCT/US2006/031982

§ 371 (c)(1),
(2), (4) Date: Aug. 1, 2008

(87) PCT Pub. No.: WO2007/022265

PCT Pub. Date: Feb. 22, 2007

(65) Prior Publication Data

US 2008/0308728 A1 Dec. 18, 2008

Related U.S. Application Data

(60) Provisional application No. 60/709,058, filed on Aug. 16, 2005.

(51) Int. Cl.
*G01N 23/00* (2006.01)
(52) U.S. Cl. .............. 250/307; 250/306; 250/309; 250/341.1; 250/341.2; 850/18; 850/32; 850/33; 850/40; 850/48

(58) Field of Classification Search ............... 250/306, 250/307, 309, 310, 340, 341.1, 341.2, 341.6, 250/363.01, 368, 492.1, 493.1; 850/6, 18, 850/32, 33, 40, 48, 60, 62, 63; 324/754, 324/765
See application file for complete search history.

(56) References Cited

U.S. PATENT DOCUMENTS 5,061,850 A 10/1991 Kelly et al.

(Continued)

OTHER PUBLICATIONS

International Search Report and Written Opinion for PCT/US2006/031982; Imago Scientific Instruments Corporation; Jan. 29, 2007; pp. 1-8.

*Primary Examiner*—Bernard E Souw
(74) *Attorney, Agent, or Firm*—Craig A. Fieschko, Esq.; DeWitt Ross & Stevens S.C.

(57) ABSTRACT

The present invention relates generally to atom probes, atom probe specimens, and associated methods. For example, certain aspects are directed toward methods for analyzing a portion of a specimen that includes selecting a region of interest and moving a portion of material in a border region proximate to the region of interest so that at least a portion of the region of interest protrudes relative to at least a portion of the border region. The method further includes analyzing a portion of the region of interest. Other aspects of the invention are directed toward a method for applying photonic energy in an atom probe process by passing photonic energy through a lens system separated from a photonic device and spaced apart from the photonic device. Yet other aspects of the invention are directed toward a method for reflecting photonic energy off an outer surface of an electrode onto a specimen.

35 Claims, 8 Drawing Sheets

U.S. PATENT DOCUMENTS

| | | | |
|---|---|---|---|
| 5,235,187 A * | 8/1993 | Arney et al. | 850/58 |
| 6,624,648 B2 * | 9/2003 | Eldridge et al. | 324/761 |
| 6,749,776 B2 * | 6/2004 | Han et al. | 252/518.1 |
| 6,956,210 B2 * | 10/2005 | Doan | 850/10 |
| 6,987,277 B2 * | 1/2006 | Baur et al. | 250/492.2 |
| 7,076,871 B2 * | 7/2006 | Horiuchi et al. | 29/857 |
| 2004/0185740 A1 * | 9/2004 | Han et al. | 445/3 |
| 2005/0077468 A1 * | 4/2005 | Baur et al. | 250/307 |
| 2005/0082475 A1 * | 4/2005 | Doan | 250/307 |
| 2006/0000814 A1 * | 1/2006 | Gu et al. | 219/121.69 |
| 2008/0296489 A1 * | 12/2008 | Olson et al. | 250/286 |
| 2009/0138995 A1 * | 5/2009 | Kelly et al. | 850/60 |

\* cited by examiner

ATOM PROBES, ATOM PROBE SPECIMENS, AND ASSOCIATED METHODS

CROSS-REFERENCE TO RELATED APPLICATION(S)

This application is a U.S. National Phase of International Application No. PCT/US06/31982, filed Aug. 15, 2006, entitled ATOM PROBES, ATOM PROBE SPECIMENS, AND ASSOCIATED METHODS, which claims the benefit of U.S. Provisional Patent Application No. 60/709,058, filed Aug. 16, 2005, entitled ATOM PROBES, ATOM PROBE SPECIMENS, AND ASSOCIATED METHODS, both of which are fully incorporated herein by reference.

TECHNICAL FIELD

Embodiments of the present invention relate to atom probes, atom probe specimens, and associated methods.

BACKGROUND

An atom probe (e.g., atom probe microscope) is a device which allows specimens to be analyzed on an atomic level. For example, a typical atom probe includes a specimen mount, an electrode, and a detector. During analysis, a specimen is carried by the specimen mount and a positive electrical charge (e.g., a baseline voltage) is applied to the specimen. The detector is spaced apart from the specimen and is negatively charged. The electrode is located between the specimen and the detector, and is either grounded or negatively charged. A positive electrical pulse (above the baseline voltage) and/or a laser pulse (e.g., photonic energy) are intermittently applied to the specimen. Alternately, a negative pulse can be applied to the electrode. Occasionally (e.g., one time in 100 pulses) a single atom is ionized near the tip of the specimen.

The ionized atom(s) separate or "evaporate" from the surface, pass though an aperture in the electrode, and impact the surface of the detector. The identity of an ionized atom can be determined by measuring its time of flight between the surface of the specimen and the detector, which varies based on the mass-to-charge ratio of the ionized atom. The location of the ionized atom on the surface of the specimen can be determined by measuring the location of the atom's impact on the detector. Accordingly, as the specimen is evaporated, a three-dimensional map of the specimen's constituents can be constructed.

Generally, when it is desired to analyze a piece of bulk material in an atom probe a portion of the material must be removed from the piece of bulk material and shaped into a needle shape with a sharp tip (e.g., a tip radius of 100 nanometers) or a micotip array. These conventional atom probe specimens are suitable for the very high concentrated electrical fields associated with evaporating ionized atom(s) from the specimen. These needle shaped specimens typically have a length of 100 microns or greater. The process of forming these needle shaped specimens can be a labor intensive process and can take a significant amount of time. Once a specimen is formed, the specimen is generally placed in the atom probe and analyzed.

SUMMARY

The present invention is directed generally toward atom probes, atom probe specimens, and associated methods. One aspect of the invention is directed toward a method for preparing a portion of a specimen for analysis in an atom probe that includes placing a specimen having a surface in an atom probe and selecting a region of interest on the surface. The surface has a border region bordering at least a portion of the region of interest. The method further includes moving a portion of material in the border region while the specimen is in the atom probe so that at least a portion of the region of interest protrudes relative to at least a portion of the border region.

Another aspect of the invention is directed toward a method for analyzing a portion of a specimen that includes placing a specimen having a surface in an atom probe and selecting a region of interest on the surface. The surface has a border region bordering at least a portion of the region of interest. The method further includes moving a portion of material in the border region while the specimen is in the atom probe so that at least a portion of the region of interest protrudes relative to at least a portion of the border region. The method still further includes initiating an atom probe evaporation process to analyze a portion of the region of interest.

Still another aspect of the invention is directed toward a method for applying photonic energy in an atom probe process that includes placing a specimen in an analysis chamber of an atom probe and applying a bias energy to at least a portion of the specimen. The method further includes using a photonic device to apply at least one photonic energy pulse to the at least a portion of the specimen by passing the at least one photonic energy pulse through a lens system. The lens system is separated from the photonic device and spaced apart from the photonic device.

Yet another aspect of the invention is directed toward an atom probe system using photonic energy that includes a specimen mount configured to carry a specimen. The system further includes a detector configured to detect ions evaporated from the specimen during an atom probe evaporation process and a photonic device configured to provide at least one photonic energy pulse to the specimen during the atom probe evaporation process. The system still further includes a lens system separated from the photonic device and spaced apart from the photonic device. The lens system is positioned so that when a specimen is carried in the specimen mount the at least one photonic energy pulse is provided to the specimen through the lens system.

Still another aspect of the invention is directed toward a method for applying photonic energy in an atom probe process that includes placing a specimen in an analysis chamber of an atom probe. The method further includes applying a bias energy to at least a portion of the specimen. The method still further includes applying a photonic energy pulse to the at least a portion of the specimen by reflecting the photonic energy pulse off an outer surface of an electrode.

Yet another aspect of the invention is directed toward an atom probe system using photonic energy that includes a specimen mount configured to carry a specimen. The system further includes a detector configured to detect ions evaporated from the specimen during an atom probe evaporation process and a photonic device configured to provide at least one photonic energy pulse to the specimen during the atom probe evaporation process. The system still further includes an electrode positioned proximate to the specimen mount. The electrode has an interior surface and an exterior surface. The exterior surface is configured to reflect the at least one photonic energy pulse. The electrode is positioned so that when a specimen is carried in the specimen mount the exterior surface will reflect the at least one photonic energy pulse provided by the photonic device onto the specimen.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

In the following description, numerous specific details are provided in order to give a thorough understanding of embodiments of the invention. One skilled in the relevant art will recognize, however, that the invention may be practiced without one or more of the specific details, or with other methods, components, materials, etc. In other instances, well known structures, materials, or operations are not shown or described in order to avoid obscuring aspects of the invention.

References throughout the specification to "one embodiment" or "an embodiment" means that a particular feature, structure, or characteristic described in connection with the embodiment is included in at least one embodiment of the present invention. Thus, the appearances of the phrase "in one embodiment" or "in an embodiment" in various places throughout the specification are not necessarily all referring to the same embodiment. Furthermore, the particular features, structures, or characteristics may be combined in any suitable manner in one or more embodiments.

Figure 1:
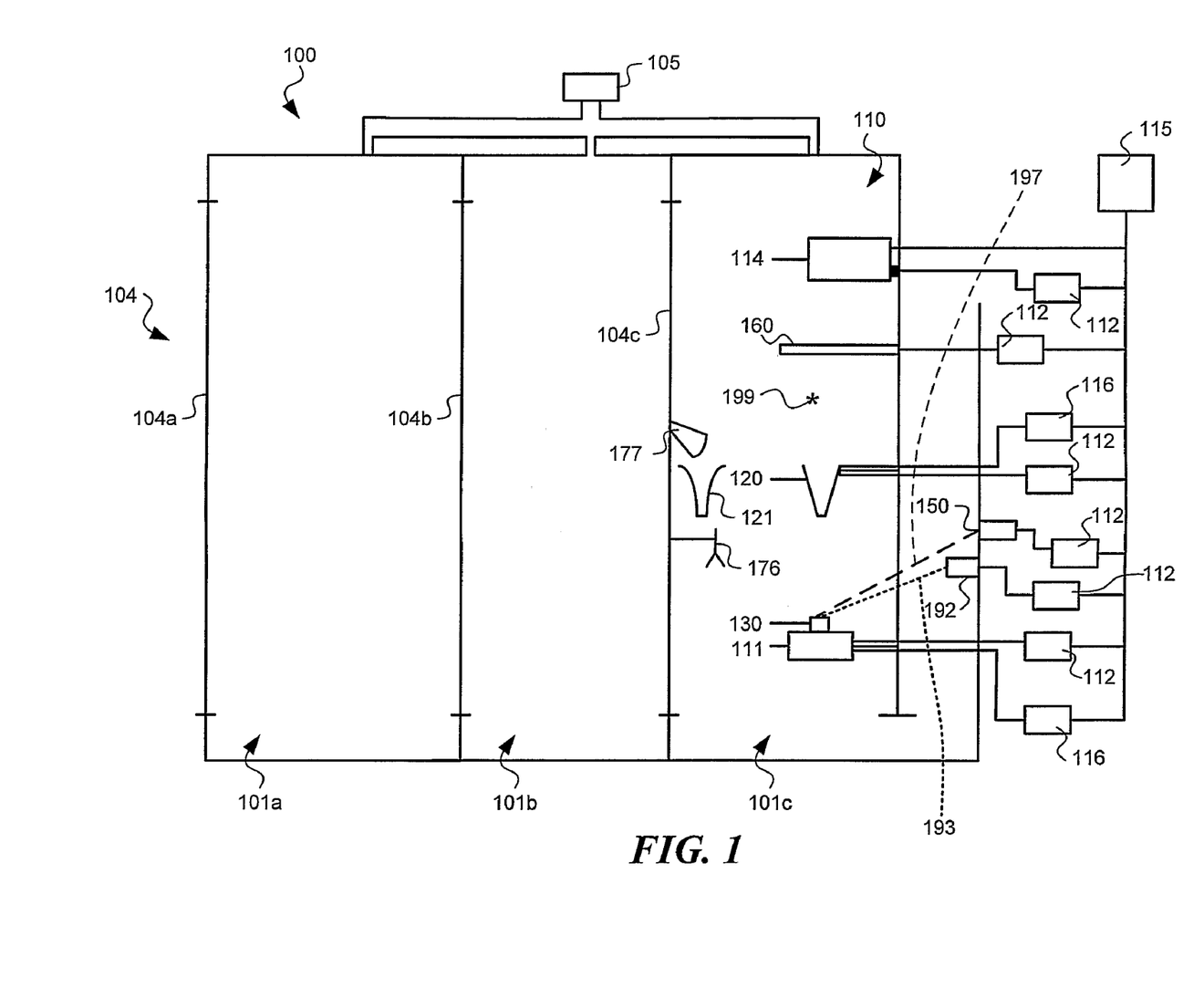
FIG. 1 is a partially schematic illustration of an atom probe device that includes an atom probe assembly with an atom probe electrode in accordance with embodiments of the invention.

FIG. 1 is a partially schematic illustration of an atom probe device 100 in accordance with embodiments of the invention. In the illustrated embodiment, the atom probe device 100 includes a load lock chamber 101a, a buffer chamber 101b, and an analysis chamber 101c (shown collectively as chambers 101). The atom probe device 100 also includes a computer 115 and an atom probe assembly 110 having a specimen mount 111, an atom probe electrode 120 (e.g., a local electrode), at least one additional atom probe electrode 121, a detector 114, a first emitting device 150 (e.g., a photonic emitting device configured to emit energy 197, including laser or photonic energy) and a second emitting device 192 (e.g., configured to emit energy 193 including X-rays, ion beams, electrons, sound waves, or the like).

The mount 111, electrode 120, detector 114, and emitting devices 150 and 192 can be operatively coupled to electrical sources 112. The electrode 120 and mount 111 can also be operatively coupled to temperature control devices 116 (e.g., cold/hot fingers that can provide contact cooling/heating to the atom probe electrode 120 and/or a specimen 130 carried by the mount 111). The additional electrode(s) 121 can be couplable to one of the electrical sources 112 and/or to one of the temperature control devices 116 (e.g., the additional electrode(s) 121 can be carried on a carousel and rotated into position to replace the electrode 120). The emitting devices 150 and 192, the detector 114, the voltage sources 112, and the temperature control devices 116 can be operatively coupled to the computer 115, which can control the analysis process, atom probe device operation, specimen preparation, data analysis, and/or an image display.

In the illustrated embodiment, each chamber 101 is operatively coupled to a fluid control system 105 (e.g., a vacuum pump, turbo molecular pump, and/or an ion pump) that is capable of lowering the pressure in the chambers 101 individually. Additionally, the atom probe device 100 can include sealable passageways 104 (e.g., gate valves) positioned in the walls of the chambers 101 that allow items to be placed in, removed from, and/or transferred between the chambers 101. In the illustrated embodiment, a first passageway 104a is positioned between the interior of the load lock chamber 101a and the exterior of the atom probe device 100, a second passageway 104b is positioned between the interior of the load lock chamber 101a and the interior of the buffer chamber 101b, and a third passageway 104c is positioned between the interior of the buffer chamber 101b and the interior of the analysis chamber 101c.

In FIG. 1, a specimen can be placed in the load lock chamber 101a via the first passageway 104a. All of the passageways 104 can be sealed and the fluid control system 105 can lower the pressure in the load lock chamber 101a (e.g., reduce the pressure to $10^{-6}$-$10^{-7}$ torr). The pressure in the buffer chamber 101b can be set at approximately the same or a lower pressure than the load lock chamber 101a. The second passageway 104b can be opened, the specimen 130 can be transferred to the buffer chamber 101b, and the second and third passageways 104b and 104c can be sealed.

The fluid control system 105 can then lower the pressure in the buffer chamber 101b (e.g., reduce the pressure to $10^{-8}$-$10^{-9}$ torr). The pressure in the analysis chamber 101c can be set at approximately the same or a lower pressure than the buffer chamber 101b. The third passageway 104c can be opened, the specimen 130 can be transferred to the analysis chamber 101c, and the third passageway 104c can be sealed. The fluid control system 105 can then reduce the pressure in the analysis chamber 101c (e.g., the pressure can be lowered to $10^{-10}$-$10^{-11}$ torr) prior to analysis of the specimen 130.

In the illustrated embodiment, the specimen 130 includes a block or sheet of bulk material. In other embodiments, the specimen 130 can include other shapes. The material can have homogenous or heterogeneous composition and can include various elements, layers, crystalline structure, grains, and the like. In FIG. 1, once the specimen is placed in the atom probe, the specimen can be prepared for analysis by selecting a region of interest on a surface of the specimen and moving a portion of material in a border region bordering the region of interest to form a depression (e.g., a moat) proximate to the region of interest.

Figure 2:
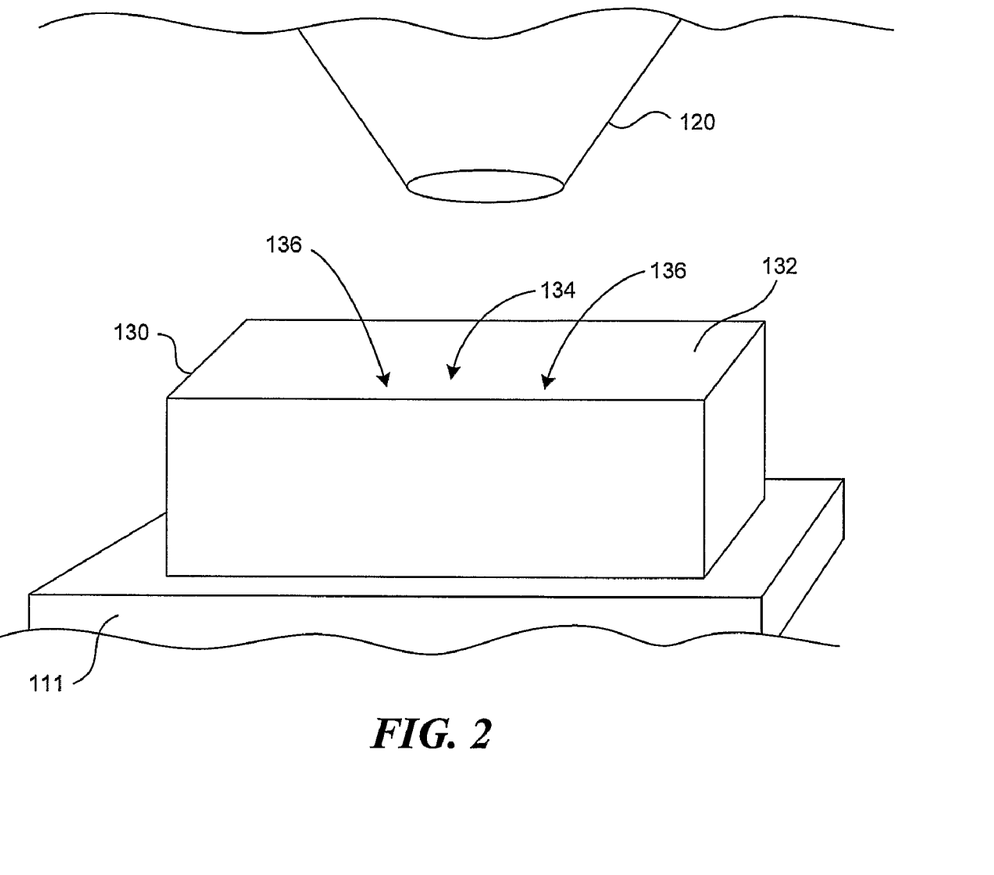
FIG. 2 is an isometric illustration of the specimen and electrode shown in FIG. 1 before material is moved in a border region in accordance with selected embodiments of the invention.

FIG. 2 is an isometric view of the specimen 130 and electrode 120 shown in FIG. 1 before material is moved in the border region 136 in accordance with selected embodiments of the invention. In FIG. 2, the specimen 130 includes a surface 132. In the illustrated embodiment, the surface is at least approximately smooth (e.g., the surface 132 can be polished, can be generally smooth with small irregularities or projections, and/or can be free of irregularities or projections). In the illustrated embodiment, the surface 132 is at least approximately flat. In other embodiments, the surface 132 can be smoothly curved. For example, in one embodiment the surface 132 can have a curved surface without sharp corners or tips (e.g., with or without small irregularities).

In the illustrated embodiment, specimen is carried by the specimen mount 111 in the analysis chamber of the atom probe. The region of interest 134 has been selected and positioned under the electrode 120. The border region 136 includes material on the surface 132 that borders the region of interest 134. As discussed above, a portion of material in the border region 136 can be moved (e.g., compressed into the specimen or removed from the specimen) so that at least a portion of the region of interest 134 protrudes relative to (e.g., above) at least a portion of the border region 136.

Figure 3:
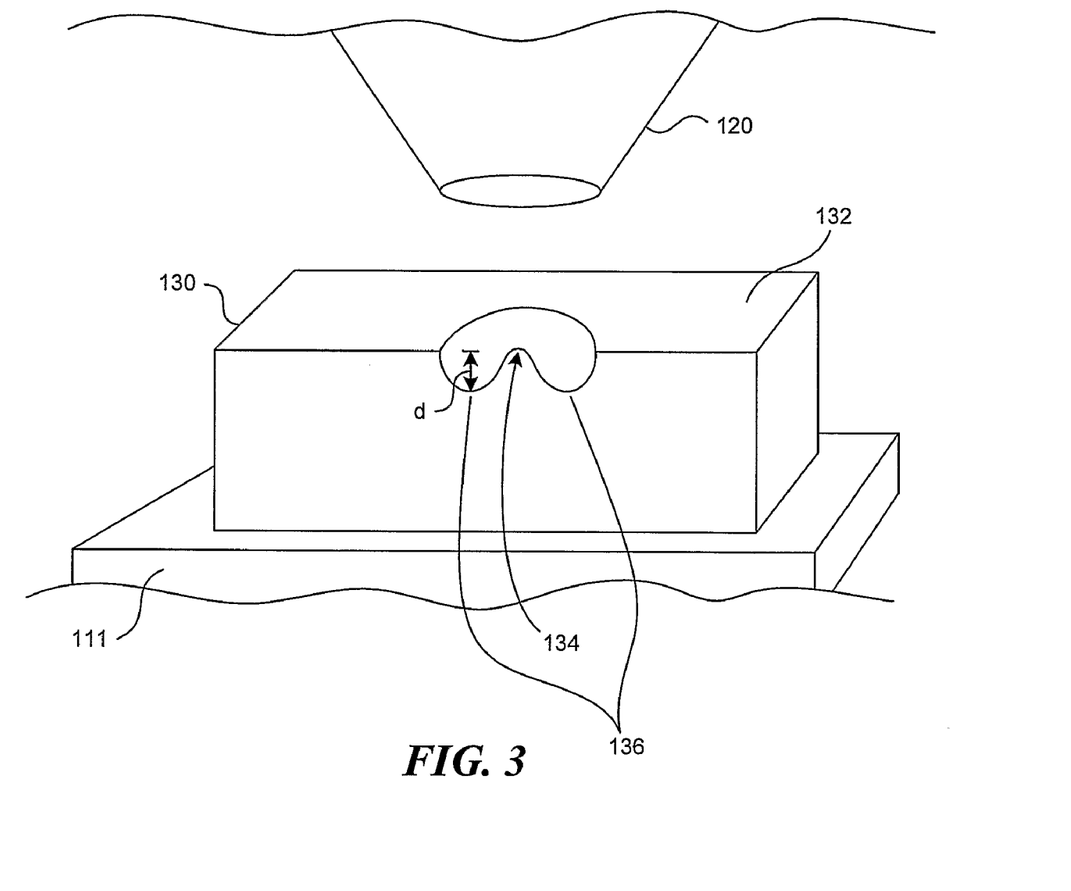
FIG. 3 is an isometric illustration of the specimen shown in FIG. 2 after material has been moved in a border region in accordance with certain embodiments of the invention.

For example, FIG. 3 is a partially schematic top planform view of the specimen 130, shown in FIG. 2, after material has been moved in a border region 136 in accordance with certain embodiments of the invention. In FIG. 3, the electrode 120 was pressed into the surface 132 (e.g., the surface as shown in FIG. 2) to create a depression proximate to the region of interest 134 by compressing material in the border region into the specimen and/or pushing aside material in the border region 136.

Because in the illustrated embodiment, the aperture of the electrode is approximately round, the region of interest was not compressed. Accordingly, in FIG. 3 at least a portion of the area of interest protrudes relative to at least a portion of the border region by at least approximately distance d. For example, in selected embodiments the distance d can be from 0.001 to 30 microns. In other embodiments the distance d can have other values. In FIG. 3, because the electrode 120 was lowered to move the portion of material in the border region and then raised, the specimen 130 is properly positioned to begin an atom probe evaporation/analysis process (e.g., analyzing the region of interest by evaporating ions). In other embodiments, the electrode 120 can be lowered to move the portion of material in the border region and the additional electrode 121 can be used during the analysis process (e.g., rotated into position after the portion of the border region is compressed).

In the illustrated embodiment, the region of interest 134 was located on the edge of the surface 132, so that there was little or no border region 136 located on one side of the region of interest 134. However, in the illustrated embodiment when the electrode 120 was pressed into the specimen 130, the portion of the region of interest positioned proximate to the edge of the surface 132 was positioned such that the electrode 120 caused the region of interest proximate to the edge of the surface 132 to have a rounded shape. In other embodiments, the electrode 120 can be positioned such that the region of interest is not rounded proximate to the edge of the surface 132 when the electrode is pressed into the specimen. In still other embodiments, the border region 136 can completely surround the region of interest 134.

Although in the illustrated embodiment a portion of material in the border region was moved while the specimen was located in the analysis chamber of the atom probe, in other embodiments the portion of material on the border region can be moved while the specimen is located in other portions of the atom probe (e.g., the load lock chamber or the buffer chamber). Additionally, in certain embodiments the electrode 120 can be vibrated as it is pressed into the surface 132 to aid in moving a portion of material in the border region. For example, in selected embodiments the electrode 120 can be vibrated ultrasonically via ultrasonic energy emitted by the second emitter 192 and/or via energy transferred to the electrode 120 via an electrode mount. In yet other embodiments, the electrode 120 can have a selected characteristic and/or a selected shape to facilitate moving a portion of material in the border region (e.g., an aperture of the electrode can include a sharp edge to better compress a portion of material in the border region).

In other embodiments, the portion of material in the border region can be moved using other methods or techniques. For example, in selected embodiments a tool (e.g., the tool 176 shown in FIG. 1) can be used to move a portion of the material in the border region. For instance, the tool can be extended and used to compress material in the border region similar to the process described above with reference to the electrode 120. In still other embodiments, photonic energy (e.g., from the first emitter 150 shown in FIG. 1) can be used to melt a portion of the material in the border region. In selected embodiments, the melted portion of material can flow or be moved to create the depression in a portion of the border region. In other embodiments, the process of melting the portion of material can change the crystalline structure of the portion of material such that the portion of material takes up less space and forms a depression in a portion of the border region.

In other embodiments, material can be removed from the at least a portion of the border area to form the depression. For example, in certain embodiments photonic energy (e.g., from the first emitter 150 shown in FIG. 1) can be used to evaporate, burn-away, and/or otherwise remove a portion of material from the border region to from a depression in a portion of the border region. In other embodiments, an ion beam (e.g., a focused or broad ion beam from the second emitter 192 shown in FIG. 1) can be used to remove a portion of material from the border region to form a depression. In still other embodiments, the tool 176, shown in FIG. 1, can include a grinding or cutting apparatus and the tool can grind or cut away a portion of material from the border region to form the depression. In yet other embodiments, the electrode 120 can be used to erode a portion of material away from the border region.

Figure 4:
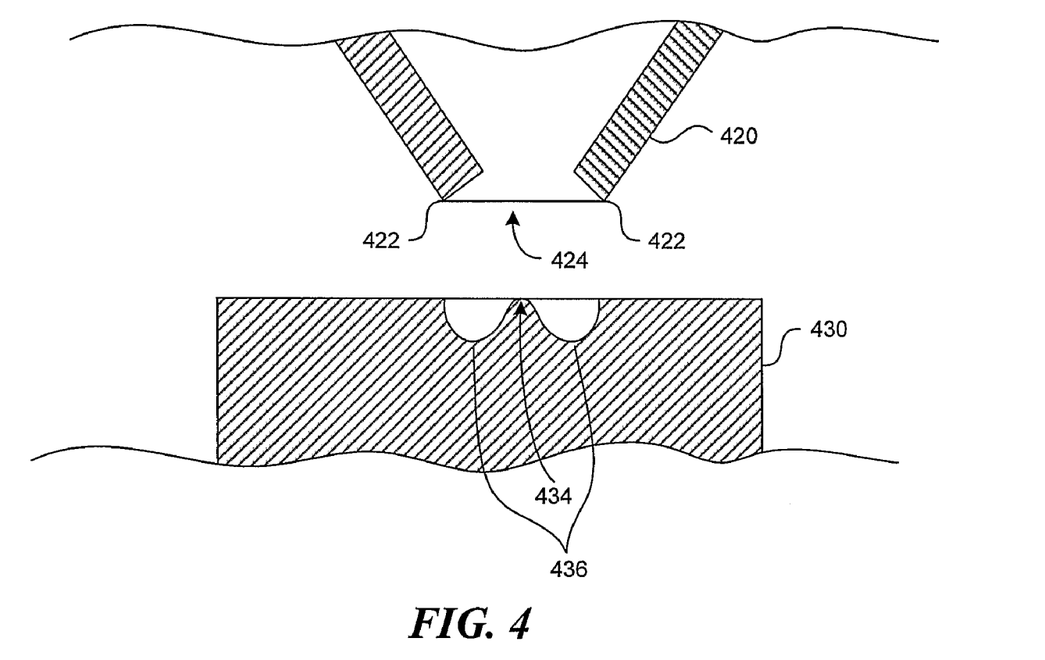
FIG. 4 is a partially schematic cross-sectional illustration of an electrode suitable for use in selected embodiments of the invention.

For example, in certain embodiments, a selected shaped local electrode and/or selected electrical profile (e.g., the characteristics of the electrical energy supplied to the electrode via a power supply) can used to erode a portion of material away from the border region. For instance, FIG. 4 is a partially schematic cross-sectional illustration of an electrode 420 having a sharp edge 422 (e.g., an annular cusp) around the aperture 424 of the electrode 420 in accordance with selected embodiments of the invention. In FIG. 4, the sharp edge 422 of the electrode is positioned over a border region 436 of a specimen 430. In the illustrated embodiment, an electrical potential can be created between a border region 436 and the electrode 420 (e.g., via power supplies coupled to the specimen 430 and the electrode 420) to erode a portion of material in the border region.

For example, in certain embodiments a positive voltage can be applied to the specimen 430 and a negative voltage can be applied to the electrode 420 or the electrode 420 can be grounded, creating an electrical field between the specimen 430 and the electrode 420. The sharp edge 422 can increase the electric field directly under the sharp edge 422 of the specimen 420. Accordingly, atoms proximate to the sharp edge 422 (e.g., in the border area 436) can be ionized and depart the specimen 430, thereby causing a portion of material to erode away from the border region 436 creating a depression proximate to a region of interest 424. In selected embodiments, once the depression is formed the region of interest can be analyzed via an atom probe analysis process using the electrode 430, using a different electrode, or using the electrode 430 transposed with (e.g., placed proximate to) another electrode. In certain embodiments where the same electrode is used for the erosion and analysis processes (e.g., using different amounts of energy and/or different types of energy), the electrode and specimen can be properly aligned for the analysis process at the completion of the erosion process without having to move the specimen.

In selected embodiments, depending on the shape of the electrode and the resulting electric field, it may be possible to erode a portion of material away from the border region by maintaining a steady electrical potential between the specimen 430 and the electrode 420. In other embodiments, a baseline potential can be maintained between the specimen 430 and the electrode 420, and additional energy can be intermittently applied to cause material to erode. For example, the positive voltage on the specimen 430 can be intermittently increased, a negative voltage on the electrode can be intermittently added or increased, and/or additional energy can be applied to the border region 436 of the specimen 430 (e.g., in the form of photonic energy, an ion beam, an electron stream, or the like) to facilitate ionization and the erosion process.

Referring back to FIG. 1, once a portion of material in the border region of the specimen 130 has been moved so that at least a portion of the region of interest protrudes relative to at least a portion of the border region, the specimen 130 can be positioned in the analysis chamber 101c (e.g., as discussed above, it may or may not have been positioned in the analysis chamber while the depression was formed). An atom probe evaporation process can then be imitated to analyze a portion of the area of interest of the specimen 130.

During this analysis process, a positive electrical charge (e.g., a bias voltage or bias energy) can be applied to the specimen. The detector can be negatively charged and the electrode can be either grounded or negatively charged. A pulse energy can be intermittently applied. For example, in selected embodiments a positive electrical pulse (e.g., an increase above the baseline energy or voltage) can be intermittently applied to the specimen 130 or a negative electrical pulse can be applied to the electrode 120. The electric field(s) created by the electrical charges can provide energy to ionize one or more atom(s) on the surface of the specimen 130. These ionized atom(s) 199 can separate or "evaporate" from the surface, pass though an aperture in the electrode 120, and impact the surface of the detector 114.

The time of flight from the region of interest of the specimen to the detector can be derived from the output of the detector 114 and the mass-to-charge ratio of the liberated ion can be inferred. Additionally, the detector 114 can include a position sensitive detector, and a position on the region of interest from where the detected ions were evaporated can be at least approximately determined based on the location where the detected ions impact the detector 114. Accordingly, as the specimen 130 is evaporated, a three-dimensional map of the specimen's constituents can be constructed.

In certain embodiments, the pulse energy can include an electrical pulse, a photonic emission, an ion beam, an electron beam or packet, and/or some other suitable pulsed energy source. For example, in a selected embodiment, laser or photonic energy from the first emitting device 150 can be used to emit an emission 197 (e.g., photons or laser light) to thermally pulse a portion of the specimen 130 to assist with the evaporation process (e.g., the removal of ionized atoms). In other embodiments, the second emitter 192 can emit an emission 193 that includes an ion beam to aid in the evaporation process.

As shown in FIG. 1, in selected embodiments a divergent or convergent ion optic 160 coupled to a power supply 112 can be interposed between the electrode 120 and the detector 114 to provide a desired affect. For example, in certain embodiments, a divergent ion optic can be used to increase the spread (spatial distribution) of the liberated ions and the detector's output signals can be further analyzed to determine the origin of the ion on the surface of the specimen/substrate. In some embodiment, this feature can provide improve position resolution.

In other embodiments, a convergent optic can be used to decrease the spread of the liberated ions to focus them onto the detector 114 (e.g., a position sensitive or a position insensitive detector). In selected embodiments, a convergent optic can be used to monitor the gross signal generated by the ion flux independent of any spatial information. In some embodiments, this can provide general information about the region of interest during a first evaporation rate. Once a desired characteristic is seen in the general information (e.g., a desired mass-to-charge ratio), the atom probe device can be transitioned to a higher resolution mode that includes a second evaporation rate and spatial information (e.g., a spatial detector). In various embodiments, the ionic optic can include various configurations and/or arrangements. For example, in selected embodiments the ionic optic can include an achromatic quadrupole multiplet. In still other embodiments, the atom probe device 100 does not include an ionic optic 160. Although in the illustrated embodiment, the ion optic is shown being used with a bulk type specimen, in other embodiments the ion optic can also be used with conventional atom probe specimens.

In yet other embodiments, the atom probe device 100 can have more, fewer, and/or other arrangements of components. For example, in certain embodiments the atom probe device 100 can include more or fewer chambers, or no chambers. In other embodiments, the atom probe device can include multiple atom probe electrodes 120 and/or electrode(s) 120 having different configurations/placements (e.g., planar electrode(s)). In still other embodiments, the atom probe device 100 can include more, fewer, or different emitting devices 150 and/or 192; more, fewer, or different temperature control systems 116; more, fewer, or different tools, and/or more, fewer, or different electrical sources 112. In still other embodiments, the atom probe device 100 can include additional detectors or sensors.

In selected embodiments, the detector 114 can be used to determine when the transition from a smooth surface to a shaped surface (e.g., wherein a portion of material from the border region has been removed to create the depression proximate to the region of interest) has occurred. For example, in certain embodiments, as the depression is formed during an erosion process, the ions leaving the specimen will tend to have divergent flight paths. Accordingly, a diameter of a spatial distribution of ions hitting the detector 114 may increase, indicating a transition to a shaped surface. In selected embodiments, this diameter of spatial distribution can be related to an at least approximate distance a portion of the region of interest protrudes relative to (e.g., above) a portion of the border region. Accordingly, this parameter can be used to determine an at least approximate distance a portion of the region of interest protrudes relative to a portion of the border region.

Other methods and parameters can be used to gauge the amount of shaping of the surface or the at least approximate distance a portion of the region of interest protrudes relative to a portion of the border region. For example, in selected embodiments, the atom probe device 100 shown in FIG. 1 can include an additional sensor 177 (e.g., a second detector or an independent scanning device such as a low energy electron microscopy (LEEM) device or photoemission electron microscopy (PEEM) device) that can be used to determine the at least approximate distance a portion of the region of interest protrudes relative to a portion of the border region. In other embodiments, when a portion of material from the border region is being eroded, the erosion process can be halted and an atom probe analysis process can be used to determine the at least approximate distance a portion of the region of interest protrudes relative to a portion of the border region. For example, when using a constant electrical potential between the electrode 120 and the specimen 130 to erode the border region of the specimen 130, the amount of shaping can be gauged by periodically decreasing the voltage and introducing a pulse energy while monitoring the detector 114. In selected embodiments, this process can be used to determine if the region of interest protrudes relative to a portion of the border an amount sufficient to support atom probe analysis.

In still other embodiments, the electrode can be used to non-invasively map out variations in the electric field on the specimen surface using field electron emission from the specimen and to provide topographical contrast in a technique similar to LEEM or PEEM. For example, in certain embodiments a negative voltage can be placed on the specimen and the electrode can be held at ground. The current generated by the field emitted electrons from the region of interest can be monitored in both the electrode 120 and the detector 114. This parameter (e.g., the monitored current) can be used to reveal the topology of the surface and as an indication of the at least approximate distance a portion of the region of interest protrudes relative to a portion of the border region. Additionally, X-rays (e.g., emitted by the second emitter 192) can be used to stimulate photoelectron emission and the resultant signal can be used to map out regional work functions.

In still other embodiments, the capacitance can be measured between the surface of the specimen and the electrode. The topography of portions of the specimen can then be determined using the relationship $d = \in A/C$, where C is the measured capacitance, d is the distance between the surface of the specimen and the electrode, $\in$ is the dielectric constant for the region between the surface and the electrode, and A is the effective cross-sectional area between the surface and a surface of the electrode. In yet another embodiment, the first emitter 150 can emit photonic energy and the additional sensor 177 can include an imaging device (e.g., a CCD camera) that monitors the reflection or diffraction of the photonic energy as the photonic energy is swept across the surface of the specimen. Changes in reflectivity or the creation of a diffraction pattern can be used to determine the topography of the specimen surface.

Accordingly, in selected embodiments a parameter associated with or related to an approximate distance a portion of the region of interest protrudes relative to a portion of the border region can be monitored as a portion of material in the border region is moved (e.g., via erosion, compression, and/or via other methods). In certain embodiments, an iterative process can then be used to establish at least approximately a desired distance a portion of the region of interest protrudes relative to a portion of the border region before the region of interest is analyzed using an atom probe evaporation process.

Figure 5:
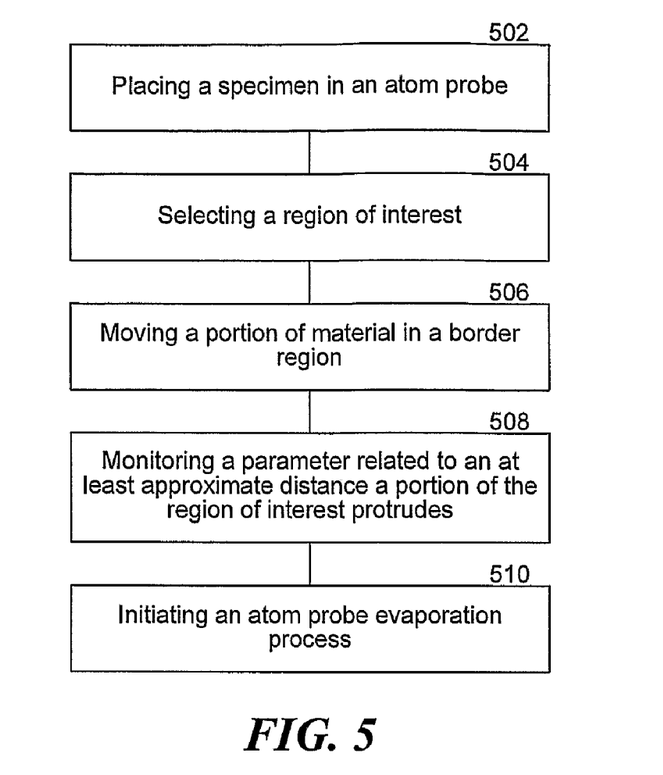
FIG. 5 is a flow diagram illustrating a process for preparing a portion of a specimen for analysis in an atom probe and analyzing the specimen in accordance with selected embodiments of the invention.

FIG. 5 is a flow diagram illustrating a process for preparing a portion of a specimen for analysis in an atom probe and analyzing the specimen in accordance with selected embodiments of the invention. The process can include placing a specimen in an atom probe (process portion 502), selecting a region of interest (process portion 504), and moving a portion of material in a border region (process portion 506). For example, in selected embodiments, placing a specimen in an atom probe can include placing a specimen that has a surface in the atom probe. Additionally, selecting a region of interest can include selecting a region of interest on the surface of the specimen and the surface can also include a border region bordering at least a portion of the region of interest. Furthermore, moving a portion of material in a border region can include moving a portion of material in the border region while the specimen is in the atom probe so that at least a portion of the region of interest protrudes relative to at least a portion of the border region. As discussed above, in certain embodiments this process can be carried out in the analysis chamber of the atom probe. In other embodiments, various components shown in FIG. 1 can be located in other atom probe chambers or portions of the atom probe and portions of the process can be carried out in other atom probe chambers or atom probe portions.

As discussed above, in selected embodiments the method shown in FIG. 5 can also include monitoring a parameter related to an at least approximate distance a portion of the region of interest protrudes (process portion 508) and/or initiating an atom probe evaporation process (process portion 510). For example, in selected embodiments monitoring a parameter related to an at least approximate distance a portion of the region of interest protrudes can include monitoring a parameter related to an at least approximate distance a portion of the region of interest protrudes relative to (e.g., above) the at least a portion of the border region. In certain embodiments, initiating an atom probe evaporation process can include initiating an atom probe evaporation process to analyze a portion of the region of interest.

In selected embodiments, some of the method discussed above can be particularly well suited for studying and/or characterizing planar structures like wafer-processed materials (e.g., such as those found in integrated electronic circuits and the read/write heads of data storage devices). For example, many of these wafer-processed materials can be particularly difficult to form into the conventional needle shaped atom probe specimens and in many cases the structures of interest exist only in a very thin layer on the surface of the wafer (e.g., some wafer processed materials include layers that are approximately 10 micrometer thick or less). By using some of the methods described above, in certain embodiments these wafer-processed materials can be analyzed without having to form conventional needle shaped atom probe specimens. Furthermore, in some embodiments a relatively uniform electric field (compared to the more focused electric field used with sharp tipped specimens) can be used to analyze the topmost layers of a given specimen.

Figure 6:
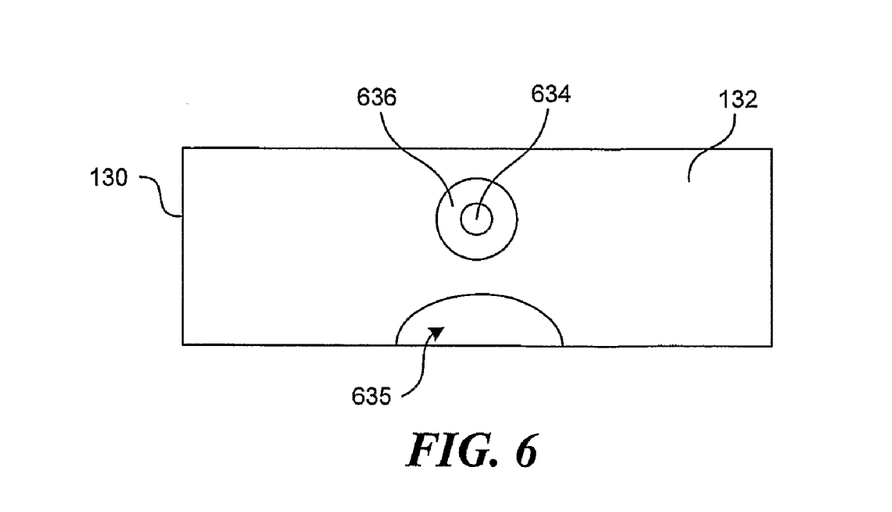
FIG. 6 is a partially schematic top plan view of the specimen shown in FIG. 1 after a first region of interest has been analyzed and after material has been moved in a new border region in accordance with certain embodiments of the invention.

Additionally, some of the method discussed above can allow an entire specimen (e.g., a bulk specimen, a wafer, or a substrate) to be introduced into an atom probe and numerous sites to be analyzed sequentially without having to repeat a pump-down-to-vacuum cycle. For example, FIG. 6 is a partially schematic illustration of the specimen 130, shown in FIG. 1, after a first region of interest (the region of interest 135 shown in FIG. 3) has been analyzed (indicated by area 635) in accordance with certain embodiments of the invention. In FIG. 6, a portion of material has been moved in a new border region 636 on the surface 132 to form a depression around a second region of interest 634 in accordance with certain embodiments of the invention. In the illustrated embodiment, the second region of interest 634 is now ready for an atom probe analysis process. In further embodiments, a third region of interest can be selected anywhere on the surface 132, a portion of material can be moved in an associated border region, and the third region of interest can be analyzed.

Figure 7:
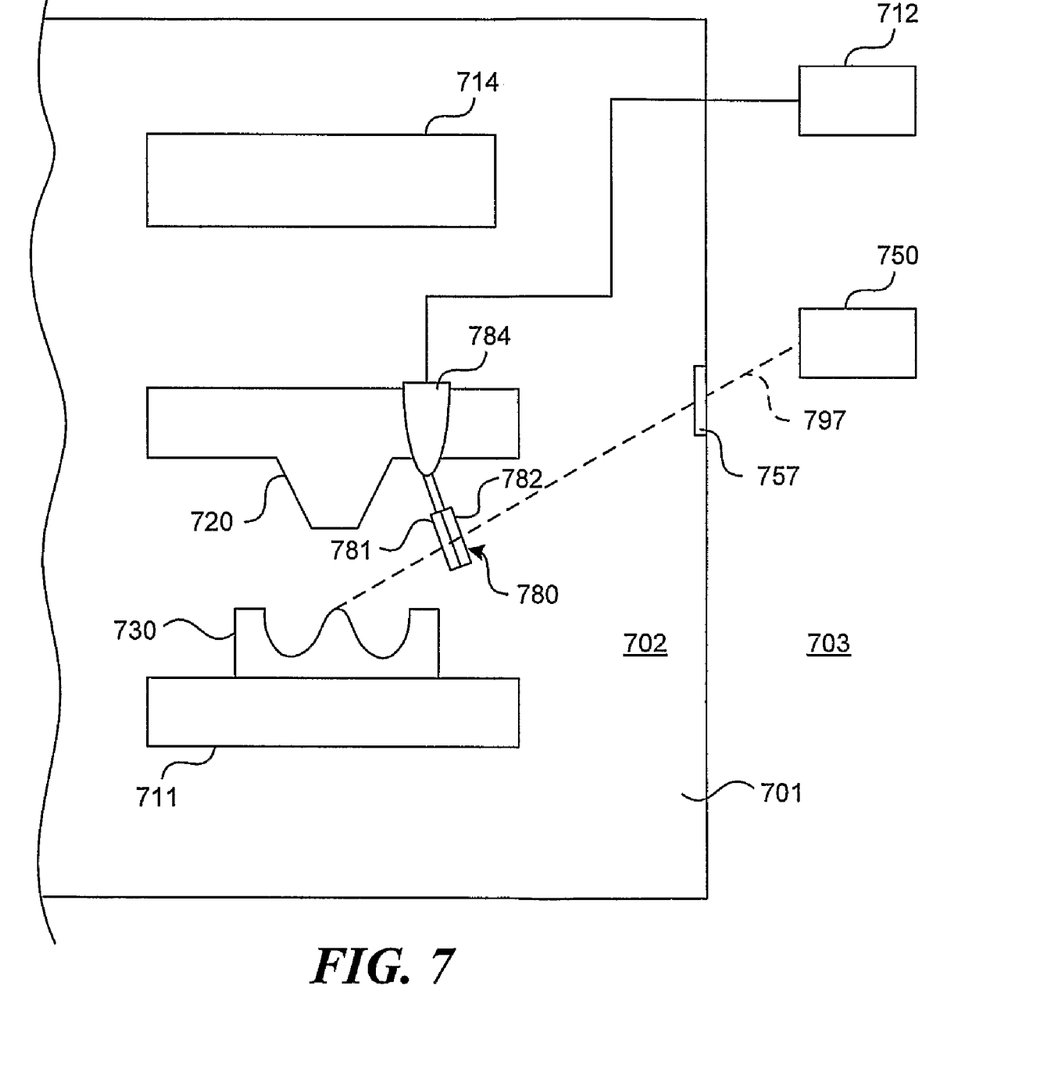
FIG. 7 is a partially schematic illustration of a portion of an atom probe device in accordance with other embodiments of the invention.

FIG. 7 is a partially schematic illustration of a portion of an atom probe device in accordance with other embodiments of the invention. In FIG. 7, a portion of an atom probe analysis chamber 701 having an interior 702 and an exterior 703 is shown. In the illustrated embodiment, a specimen mount 711 configured to carry a specimen 730 is carried in the interior 702 of the analysis chamber 701. In FIG. 7, the specimen 730 is shown being carried by the specimen mount 711. In the illustrated embodiment, a detector 714 is configured to detect ions evaporated from the specimen 730 during an atom probe evaporation process is also located in the analysis chamber 701. In FIG. 7, a photonic device 750 configured to provide at least one photonic energy pulse to the specimen 730 during the atom prove evaporation process is located in the exterior 703 of the analysis chamber 701. In the illustrated embodiment, the photonic device 750 is positioned to emit photonic energy through a window 757 in the wall of the analysis chamber 701. In other embodiments, the photonic device 750 can be located in the interior 702 of the analysis chamber 701.

In the illustrated embodiment, a lens system 780 is proximate to an electrode 720 (e.g., a local electrode). In FIG. 7, an actuator 784 couples the lens system 780 to the electrode 720. The lens system 780 includes two lenses, shown as a first lens 781 and a second lens 782. In other embodiments, the lens system 780 can have more or fewer lenses.

The actuator 784 is configured to move the first and second lenses 781 and 782 both together as a unit and separately relative to one another. The actuator 784 and the lens system 780 are located in the interior of the analysis chamber 701. For example, unlike the window 757 which has a portion that is on, exposed to, or in the exterior 703 of the analysis chamber 701, the lens system 780 is located fully within the analysis chamber 701. A power supply 712 is coupled to the actuator 784 and/or the lens system 780. In selected embodiments, the power supply and/or the actuator can be controlled by a computer, processor, or controller similar to the computer shown in FIG. 1. In the illustrated embodiment, the lens system 784 is separated from the photonic device and spaced apart from the photonic device (e.g., separate from the photonic device). The actuator is configured to position the lens system so that the at least one photonic energy pulse is provided to the specimen through the lens system. In other embodiments, the lens system can be coupled to other portions of the atom probe device, is not coupled to an actuator (e.g., has a fixed or manually adjustable position), and/or is not proximate to the electrode 720. For example, in other embodiments the lens system can be located in the wall of the analysis chamber or located exterior to the analysis chamber.

In various embodiments, the lens system 780 can be configured to perform various functions. For example, in selected embodiments, the lens system 780 can be configured to concentrate photonic energy passing through the lens system 780 (e.g., cause the photonic energy to converge toward a point), diffuse photonic energy passing through the lens system 780 (e.g., cause the photonic energy to diverge), to polarize photonic energy passing through the lens system 780, and/or to steer photonic energy passing through the lens system 780 (e.g., tilt a portion of the lens system to aim photonic energy toward or away from a portion of the specimen). In still other embodiments, the lens system can be configured to reduce an amount of photonic energy that pass through the lens system. For example, in certain embodiments the transmissivity of at least a portion of the lens system can be dependent on an amount of electrical power received from the power supply 712. Although the specimen 730 shown in FIG. 7 includes a bulk type specimen similar to those discussed above with reference to FIGS. 2-6, in other embodiments the specimen 730 can include a conventional needle shaped atom probe specimen.

Some of the embodiments discussed above can be useful for positioning a photonic pulse on a precise portion of a region of interest of a specimen and/or to a portion of a border region. Additionally, some of the embodiments discussed above can be useful in controlling the amount of photonic energy that hits a specimen. For example, some of the embodiments discussed above can be useful in controlling the amount of photonic energy that hits a specimen when controlling an evaporation process as discussed in PCT Application No. PCT/USO6/29324, filed Jul. 28, 2006, entitled ATOM PROBE EVAPORATION PROCESSES, which is fully incorporated herein by reference.

Figure 8:
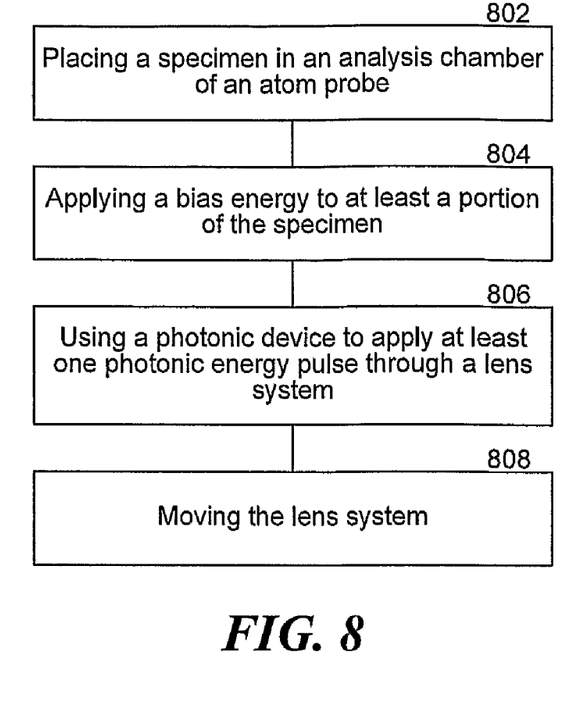
FIG. 8 is a flow diagram illustrating a process for applying photonic energy in an atom probe process in accordance with certain embodiments of the invention.

FIG. 8 is a flow diagram illustrating a process for applying photonic energy in an atom probe process in accordance with certain embodiments of the invention. The process includes placing a specimen in an analysis chamber of an atom probe (process portion 802), applying a bias energy to at least a portion of the specimen (process portion 804), and using a photonic device to apply at least one photonic energy pulse through a lens system (process portion 806). In selected embodiments, using a photonic device to apply at least one photonic energy pulse through a lens system can include applying the at least one photonic energy pulse to the at least a portion of the specimen through a lens system, wherein the lens system is separated from the photonic device and spaced apart from the photonic device. In further embodiments, the process can also include moving the lens system (process portion 808), for example, moving the lens system with an actuator prior to using the photonic device to apply the at least one photonic energy pulse to the at least a portion of the specimen.

Figure 9:
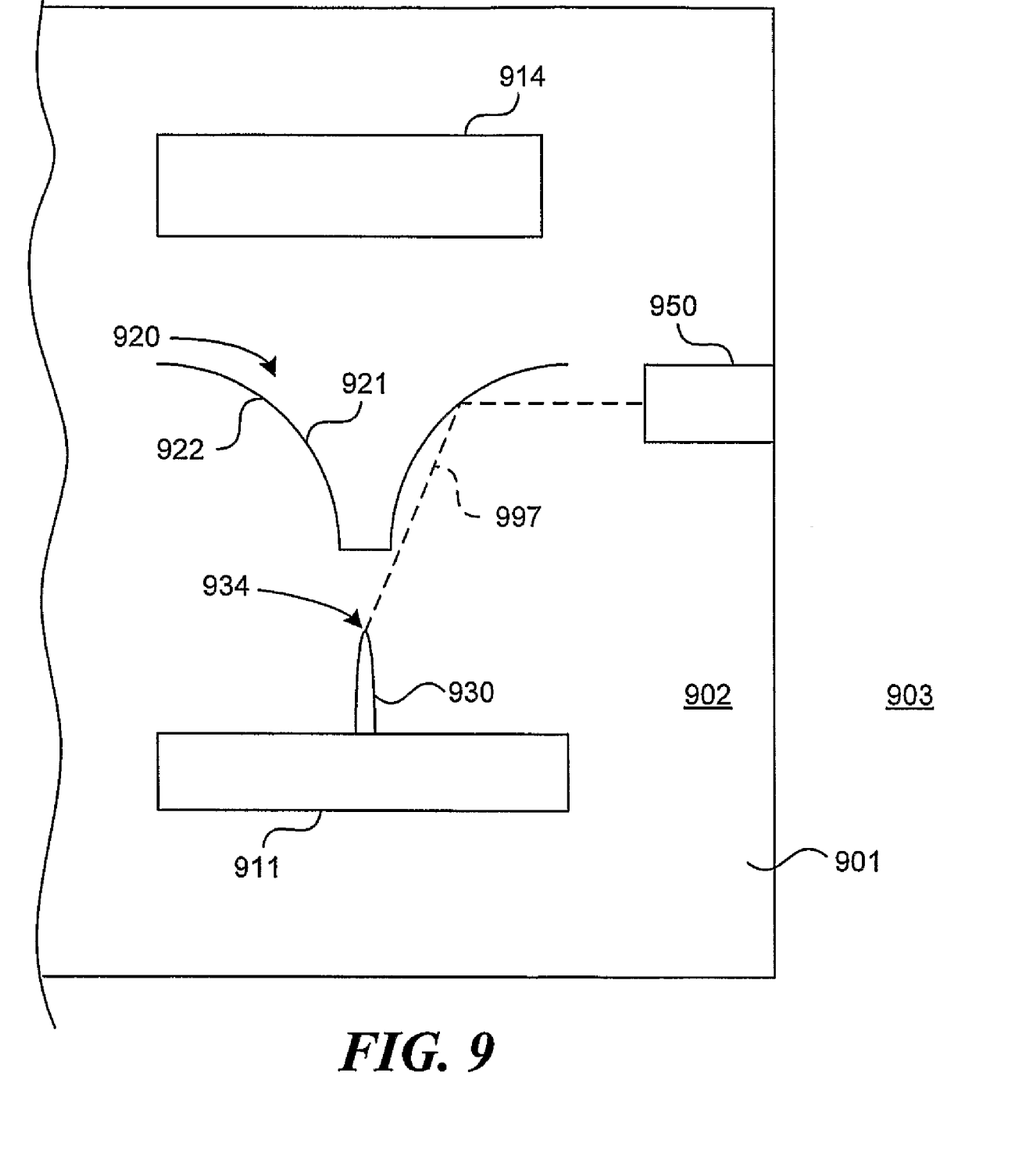
FIG. 9 is a partially schematic illustration of a portion of an atom probe device in accordance with still other embodiments of the invention.

FIG. 9 is a partially schematic illustration of a portion of an atom probe device or system in accordance with still other embodiments of the invention. In FIG. 9, a specimen mount 911 is located in the interior 902 of an atom probe analysis chamber 901. In the illustrated embodiment, the specimen mount 911 carries a specimen 930 having a region of interest 934. In FIG. 9, a detector 914 for detecting ions evaporated from the specimen 930 during an atom probe evaporation process is located in the interior of the analysis chamber 901.

In the illustrated embodiment, a photonic device 950 to provide at least one photonic energy pulse 997 to the specimen 930 during the atom probe evaporation process is also located in the analysis chamber 901. In other embodiments, the photonic device 950 is located in/on the exterior 903 of the analysis chamber 901 in a manner similar to that discussed above with reference to FIG. 7. In FIG. 9, an electrode 920 (e.g., a local electrode) is positioned proximate to the specimen mount 911. In the illustrated embodiment, the electrode 920 includes an interior surface 921 and an exterior surface 922 facing at least approximately opposite the interior surface 921. In FIG. 9, the interior surface 921 is facing generally (e.g., at least approximately) away from the specimen 930 and the exterior surface 922 is facing generally (e.g., at least approximately) toward the specimen 930. The exterior surface 922 in the illustrated embodiment is configured to reflect the at least one photonic energy pulse 997 and the electrode 920 is positioned so that the exterior surface 922 will reflect the at least one photonic energy pulse 997 provided by the photonic device 950 onto the specimen 930.

Although the specimen 930 is shown as a conventional needle shaped atom probe specimen, in other embodiments the specimen 930 can include a bulk type specimen similar to those discussed above with reference to FIGS. 2-6. In selected embodiments, the electrode 920 can be positioned to reflect the photonic energy 997 onto the region of interest 934 of the specimen, onto a border region of the specimen, and/or onto other portions of the specimen. In selected embodiments, when an analysis chamber carries multiple electrodes, different electrodes can have different reflective characteristics (e.g., the exterior surfaces can have different levels of reflectivity and/or can reflect photonic energy in different directions).

Figure 10:
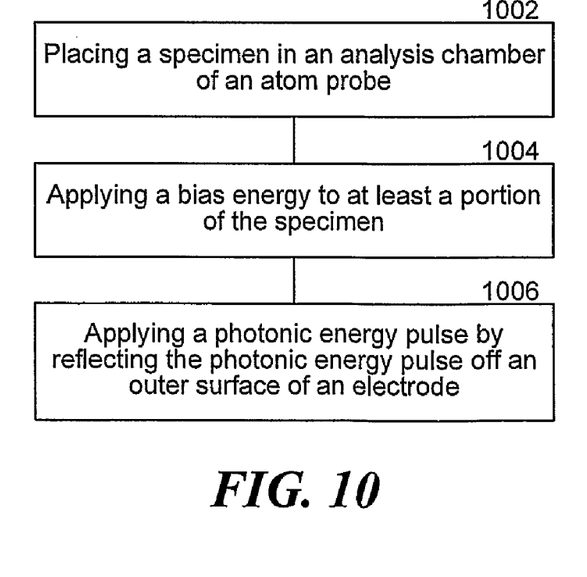
FIG. 10 is a flow diagram illustrating a process for applying photonic energy in an atom probe process in accordance with selected embodiments of the invention.

FIG. 10 is a flow diagram illustrating a process for applying photonic energy in an atom probe process in accordance with selected embodiments of the invention. The process includes placing a specimen in an analysis chamber of an atom probe (process portion 902), applying a bias energy to at least a portion of the specimen (process portion 904), and applying a photonic energy pulse by reflecting the photonic energy pulse off an outer surface of an electrode (process portion 906). For example, in selected embodiments, the reflected photonic energy can be applied to at least a portion of a specimen.

From the foregoing, it will be appreciated that specific embodiments of the invention have been described herein for purposes of illustration, but that various modifications may be made without deviating from the invention. Additionally, aspects of the invention described in the context of particular embodiments may be combined or eliminated in other embodiments. Although advantages associated with certain embodiments of the invention have been described in the context of those embodiments, other embodiments may also exhibit such advantages. Additionally, not all embodiments need necessarily exhibit such advantages to fall within the scope of the invention. Accordingly, the invention is not limited except as by the appended claims.

We claim:

1. A method for preparing a portion of a specimen for analysis in an atom probe, comprising:
    placing a specimen having a surface in an atom probe;
    selecting a region of interest on the surface, the surface having a border region bordering at least a portion of the region of interest; and
    moving a portion of material in the border region while the specimen is in the atom probe so that at least a portion of the region of interest protrudes relative to at least a portion of the border region.

2. The method of claim 1 wherein the border region surrounds the region of interest.

3. The method of claim 1 wherein the surface includes an at least approximately smooth surface.

4. The method of claim 1 wherein moving a portion of material includes moving a portion of material in the border region so that at least a portion of the region of interest protrudes away from the specimen between 0.001 and 30 microns relative to the at least a portion of the border region on the surface of the specimen.

5. The method of claim 1 wherein moving a portion of material in the border region includes removing a portion of material from the border region.

6. The method of claim 1 wherein moving a portion of material in the border region includes removing a portion of material from the border region via at least one of grinding the portion of material away from the border region, eroding the portion of material away from the border region, removing a portion of material in the border region using photonic energy, and removing material from the border region using an ion beam.

7. The method of claim 1 wherein moving a portion of material in the border region includes removing a portion of material from the border region by using a local electrode to erode a portion of material away from the border region.

8. The method of claim 1 wherein the method further comprises monitoring a parameter related to an at least approximate distance the at least a portion of the region of interest protrudes relative to the at least a portion of the border region.

9. The method of claim 1 wherein moving a portion of material in the border region includes at least one of compressing a portion of material in the border region and melting a portion of material in the border region.

10. The method of claim 1 wherein moving a portion of material in the border region includes using a local electrode to compress a portion of material in the border region.

11. The method of claim 1 wherein placing a specimen in an atom probe includes placing a specimen in the analysis chamber of an atom probe and moving a portion of material includes moving a portion of material in the border region while the specimen is in the analysis chamber.

12. A method for analyzing a portion of a specimen, comprising:
    placing a specimen having a surface in an atom probe;
    selecting a region of interest on the surface, the surface having a border region bordering at least a portion of the region of interest;
    moving a portion of material in the border region while the specimen is in the atom probe so that at least a portion of the region of interest protrudes away from the specimen relative to at least a portion of the border region; and
    initiating an atom probe evaporation process to analyze a portion of the region of interest.

13. The method of claim 12 wherein initiating an atom probe evaporation process to analyze a portion of the region of interest includes:
    applying a bias energy to at least a portion of the specimen;
    applying pulse energy to at least a portion of the specimen; and
    detecting ions using a detector.

14. The method of claim 12 wherein initiating an atom probe evaporation process to analyze a portion of the region of interest includes:
    applying a bias energy to at least a portion of the specimen;
    applying pulse energy to at least a portion of the specimen;
    detecting ions evaporated from the region of interest using a detector; and
    determining at least one of at least approximately a mass-to-charge ratio of each detected ion and an at least approximately a position on the region of interest from where each detected ion was evaporated.

15. The method of claim 12 wherein initiating an atom probe evaporation process to analyze a portion of the region of interest includes:
   applying a bias energy to at least a portion of the specimen; and
   applying pulse energy to at least a portion of the specimen, at least a portion of the pulse energy including at least one photonic energy pulse from a photonic device, the at least one photonic energy pulse passing through a lens system, the lens system being separated from the photonic device and spaced apart from the photonic device.

16. The method of claim 12 wherein initiating an atom probe evaporation process to analyze a portion of the region of interest includes:
   applying a bias energy to at least a portion of the specimen; and
   applying pulse energy to at least a portion of the specimen, at least a portion of the pulse energy including at least one photonic energy pulse, the at least one photonic energy pulse being reflected off an exterior surface of an electrode.

17. The method of claim 12 wherein initiating an atom probe evaporation process to analyze a portion of the region of interest includes:
   applying a bias energy to at least a portion of the specimen;
   applying pulse energy to at least a portion of the specimen;
   evaporating ions from the portion of the region of interest; and
   using an ion optic to influence a flight path of at least a portion of the evaporated ions as the at least a portion of the evaporated ions travel between the portion of the region of interest and a detector.

18. The method of claim 12 wherein initiating an atom probe evaporation process includes using a detector to detect ions evaporated from the region of interest of the specimen and wherein the method further includes using the detector to monitor a parameter related to an at least approximate distance the at least a portion of the region of interest protrudes relative to the at least a portion of the border region after moving a portion of material in the border region.

19. A method for applying photonic energy in an atom probe process, comprising:
   placing a specimen in an analysis chamber of an atom probe;
   applying a bias energy to at least a portion of the specimen; and
   using a photonic device to apply at least one photonic energy pulse to the at least a portion of the specimen by passing the at least one photonic energy pulse through a lens system, the lens system being separated from the photonic device and spaced apart from the photonic device.

20. The method of claim 19 wherein using a photonic device includes using a photonic device located outside of the analysis chamber and wherein the lens system is located fully within the analysis chamber.

21. The method of claim 19 wherein the method further comprises moving the lens system with an actuator prior to using the photonic device to apply the at least one photonic energy pulse to the at least a portion of the specimen.

22. The method of claim 19 wherein the lens system is configured to at least one of concentrate photonic energy passing through the lens system, diffuse photonic energy passing through the lens system, polarize the photonic energy passing through the lens system, and steer photonic energy passing through the lens system.

23. The method of claim 19 wherein the lens system is at least one of coupled to a local electrode and located proximate to the local electrode.

24. The method of claim 19 wherein using a photonic device includes using a photonic device located outside of the analysis chamber and wherein the lens system is located fully within the analysis chamber, the lens system being configured to reduce an amount of photonic energy that pass through the lens system.

25. An atom probe system using photonic energy, comprising:
   a specimen mount configured to carry a specimen;
   a detector configured to detect ions evaporated from the specimen during an atom probe evaporation process;
   a photonic device configured to provide at least one photonic energy pulse to the specimen during the atom probe evaporation process; and
   a lens system separated from the photonic device and spaced apart from the photonic device, the lens system being positioned so that when a specimen is carried in the specimen mount the at least one photonic energy pulse is provided to the specimen through the lens system.

26. The system of claim 25, further comprising an atom probe analysis chamber wherein the photonic device is positioned outside of the analysis chamber, and wherein the lens system is located fully within the analysis chamber.

27. The system of claim 25, further comprising an actuator coupled to the lens system, the actuator being configured to position the lens system.

28. The system of claim 25 wherein the lens system is configured to at least one of concentrate photonic energy passing through the lens system, diffuse photonic energy passing through the lens system, polarize photonic energy passing through the lens system, and steer photonic energy passing through the lens system.

29. The system of claim 25 wherein the lens system is at least one of coupled to a local electrode and located proximate to the local electrode.

30. The system of claim 25, further comprising an atom probe analysis chamber wherein the photonic device is positioned outside of the analysis chamber and the lens system is located fully within the analysis chamber, the lens system being configured to reduce an amount of photonic energy that passes through the lens system.

31. A method for applying photonic energy in an atom probe process, comprising:
   placing a specimen in an analysis chamber of an atom probe;
   applying a bias energy to at least a portion of the specimen; and
   applying a photonic energy pulse to the at least a portion of the specimen by reflecting the photonic energy pulse off an outer surface of an electrode.

32. The method of claim 31 wherein the electrode includes a local electrode.

33. An atom probe system using photonic energy, comprising:
   a specimen mount configured to carry a specimen;
   a detector configured to detect ions evaporated from the specimen during an atom probe evaporation process;
   a photonic device configured to provide at least one photonic energy pulse to the specimen during the atom probe evaporation process; and an electrode positioned proximate to the specimen mount, the electrode having an interior surface and an exterior surface, the exterior surface being configured to reflect the at least one photonic energy pulse, the electrode being positioned so that when a specimen is carried in the specimen mount the exterior surface will reflect the at least one photonic energy pulse provided by the photonic device onto the specimen.

34. The system of claim 33 wherein the electrode is a local electrode.

35. The system of claim 33 wherein the specimen mount is configured to carry a specimen having a region of interest, and wherein the electrode is positioned so that the exterior surface will reflect the at least one photonic energy pulse onto the region of interest of the specimen when the specimen is carried by the specimen mount.

* * * * *